United States Patent [19]

Kielland

[11] Patent Number: 5,683,286

[45] Date of Patent: Nov. 4, 1997

[54] BREAST PAD FOR NURSING MOTHERS

[76] Inventor: Laura J. Kielland, 13905 SE. 155th Pl., Renton, Wash. 98058

[21] Appl. No.: 530,947

[22] Filed: Sep. 20, 1995

[51] Int. Cl.$^6$ ............................................. A41D 27/26
[52] U.S. Cl. .............................. 450/37; 450/57; 2/267
[58] Field of Search ............................. 450/37, 53, 54, 450/55, 56, 57; 2/267, 268, 73, 243.1, 244

[56] References Cited

U.S. PATENT DOCUMENTS

| | | | |
|---|---|---|---|
| 2,891,544 | 6/1959 | London | 450/37 X |
| 2,896,623 | 7/1959 | Fitzgerald | 2/267 |
| 3,442,268 | 5/1969 | Bird | 2/267 |
| 4,074,721 | 2/1978 | Smits et al. | 450/37 X |
| 4,674,510 | 6/1987 | Sneider | 450/57 |

*Primary Examiner*—Jeanette E. Chapman
*Attorney, Agent, or Firm*—Joan H. Pauly

[57] ABSTRACT

The body (2) of a breast pad has absorbent portions (4) and shaping portions (6). The absorbent portions (4) include a center portion (8) and a plurality of radially extending lobes (10). The shaping portions include a plurality of triangular sections (6) that extend radially inwardly from the perimeter of the body (2) to the center portion (8). The body (2) folds along the sections (6) from a flat pre-use configuration into a convex use configuration to maintain a substantially uniform thickness of the absorbent portions (4).

6 Claims, 1 Drawing Sheet

BREAST PAD FOR NURSING MOTHERS

TECHNICAL FIELD

This invention relates to breast pads for nursing mothers and, more particularly, to such a pad that has absorbent portions and thinner shaping portions extending between the absorbent portions to permit the pad to be folded along the shaping portions to conform to the shape of a breast while maintaining a substantially uniform thickness.

BACKGROUND INFORMATION

In recent years, women have become increasingly active outside the home and in various work environments. Maternity leaves from employment following the birth of a child are commonly quite short. At the same time, the popularity of breast feeding babies has experienced a resurgence. In order to prevent staining of clothing and embarrassment caused by leaking of fluid, nursing mothers employ pads to absorb leaking fluid. Such pads are commonly placed inside a bra. Conventionally, the pads that are employed are flat with no contouring. Such flat pads do not conform to the shape of a breast and are of uneven thickness when placed inside a bra. The folding of the pad necessary to put it into position results in a lumpy uneven outer surface that is uncomfortable and at times unsightly.

SUMMARY OF THE INVENTION

The present invention is directed toward an improved breast pad for nursing mothers. According to an aspect of the invention, the pad comprises a pad body having absorbent portions and shaping portions. The absorbent portions have a first thickness, and the shaping portions have a second thickness that is less than the first thickness. The absorbent portions include a center portion of the pad body and a plurality of lobes extending radially outwardly from the center portion. The shaping portions include a plurality of sections extending radially inwardly from an outer edge of the pad body between the lobes, with one section being between each pair of adjacent lobes. The body has a substantially flat pre-use configuration. The sections are sized and shaped and have sufficient flexibility to allow the body to be folded along the sections to shape the body into a convex use configuration which substantially conforms to the shape of a breast. In the use configuration, the absorbent portions are maintained at a substantially uniform thickness.

The breast pad of the invention may be made from various materials. Preferably, the pad body comprises a permeable layer, a substantially waterproof layer, and absorbent material. First portions of the permeable and waterproof layers are laminated to each other to form the shaping portions. Second portions of the layers have absorbent material sandwiched therebetween to form the absorbent portions. A preferred feature of a pad made from these types of materials is a body that includes a nonabsorbent perimeter surrounding the absorbent portions and formed by edge portions of the layers that are laminated to each other.

The details of the configuration of the pad may be varied. In the preferred embodiment, each section of the shaping portions is substantially triangular and tapers radially inwardly from a perimeter portion of the body to the center portion. The sections are preferred arranged in a plurality of opposite pairs. Regardless of the types of material that are used in the construction of the pad and the details of the pad configuration, the pad preferably has a nonabsorbent perimeter to inhibit wicking of moisture to clothing.

The invention solves the problems discussed above in relation to the type of pad conventionally used by nursing mothers. Pads constructed according to the invention are easily shaped into a use configuration that conforms to the shape of a breast and has a substantially uniform thickness. Thus, the pads are both easy to use and provide a more satisfactory result. In use, the pad maintains a smooth outer contour of a bra and clothing worn over the bra to avoid calling attention to the fact that the user is a nursing mother. This increases the emotional comfort as well as the physical comfort of the user. In addition, the substantially uniform thickness of the use configuration of the pad helps to maximize its effectiveness as an absorbing material by encouraging uniform absorption of fluid around the circumference of the pad.

The advantages and features discussed above and other advantages and features will become apparent from the detailed description of the best mode for carrying out the invention that follows.

BRIEF DESCRIPTION OF THE DRAWINGS

In the drawings, like element designations refer to like parts throughout, and.

BEST MODE FOR CARRYING OUT THE INVENTION

Figure 1:
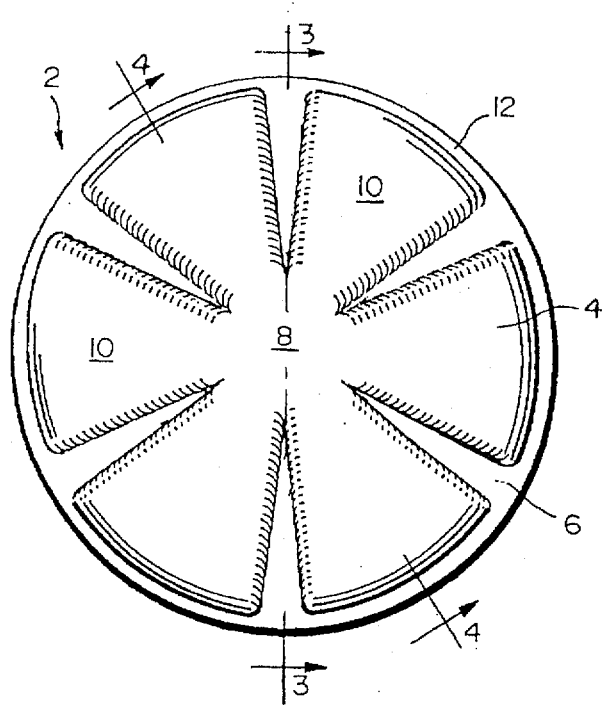
FIG. 1 is an elevational view looking at the outer surface of the preferred embodiment of the pad when the pad is in its pre-use flat configuration.
Figure 3:
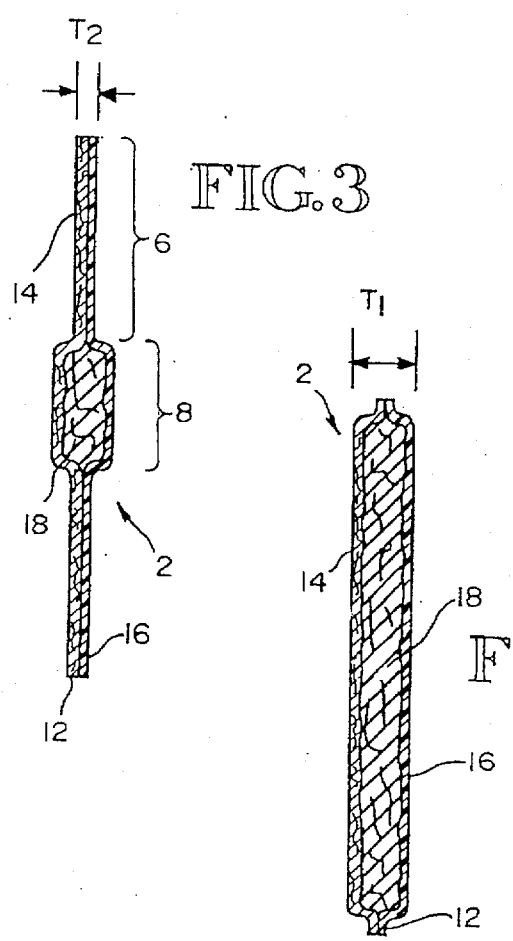
FIGS. 3 and 4 are sectional views taken along the lines 3—3 and 4—4, respectively, in FIG. 1.
Figure 4:
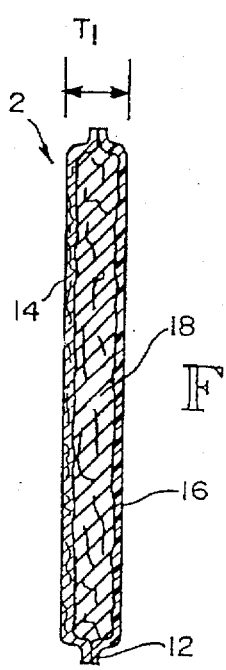

The drawings show a pad 2 that is constructed according to the invention and that also constitutes the best mode for carrying out the invention currently known to the applicant. The illustrated pad has an integral body 2 with absorbent portions 4 and shaping portions 6. Referring to FIGS. 1, 3, and 4, the pad body 2 has a substantially flat pre-use configuration in which the absorbent portions 4 have a first substantially uniform thickness $T_1$ and the shaping portions 6 have a second thickness $T_2$ that is less than the first thickness $T_1$.

As can best be seen in FIG. 1, the absorbent portions 4 of the body 2 include a center portion 8 of the body 2 and a plurality of lobes 10 extending radially outwardly from the center portion 8. In the pre-use configuration, the absorbent portions 4 have an appearance resembling a six-leaf clover. A flat edge portion 12 extends around the perimeter of the body 2 to form a nonabsorbent perimeter 12. The shaping portions 6 of the body 2 comprise a plurality of substantially triangular, or pie-shaped sections 6 that taper radially inwardly from the perimeter 12 to the center portion 8. As shown, the sections 6 are arranged in three opposite pairs, with one nonabsorbent shaping section 6 being between each pair of adjacent lobes 10 of the absorbent portions 4.

Referring to FIGS. 3 and 4, the pad body 2 is made from a plurality of materials, including a permeable layer 14, a substantially waterproof layer 16, and absorbent material 18. These materials are preferably the same types of materials that are commonly found in disposable diapers. The permeable layer 14 is a wood fiber product permeable material. The outer substantially waterproof layer 16 is a thin layer of plastic. The absorbent material 18 is preferably a material such as polyacrylate filler. The two layers 14, 16 are laminated to each other to form the shaping portions 6 and the perimeter 12. The laminated perimeter 12 extends all the way around the circumference of the pad body 2 and surrounds the absorbent portions 4 to prevent wicking of moisture to clothing. In the absorbent portions 4 of the pad 2, the two layers 14, 16 have absorbent material 18 sandwiched therebetween.

Figure 2:
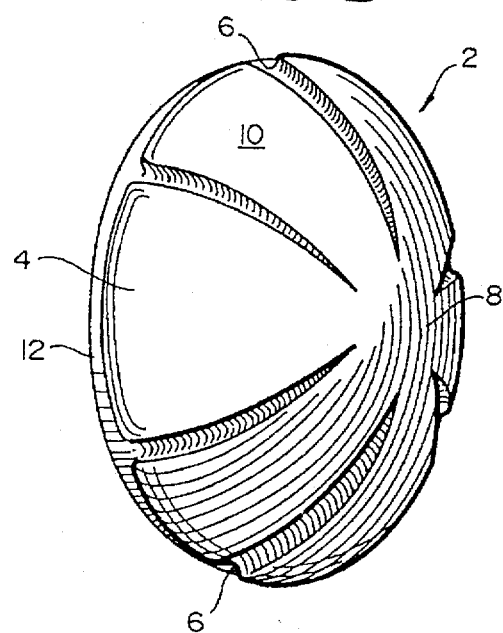
FIG. 2 is a pictorial view of the pad in a convex use configuration.

In use, the pad body 2 is placed on a breast or into the cup of a bra and gently pressed into position. The pad body 2 naturally folds along the triangular shaping sections 6 to mold and shape the body 2 into a convex use configuration. The sections 6 have sufficient flexibility so that the body 2 will easily fold along the sections 6 when subjected to a gentle molding pressure. The sections 6 are sized and shaped to allow the folding action. In the preferred embodiment shown in the drawings, the dimensioning and configuration of the sections 6 is maximized to maximize the ease of use and overall efficiency of the pads 2. The pad body 2 is molded into a convex use configuration, such as the configuration shown in FIG. 2, that substantially conforms to the shape of a breast. In the use configuration, the absorbent portions 4 of the pad 2 are maintained at a substantially uniform thickness $T_1$ to obtain the advantageous aesthetic and functional characteristics discussed above.

Although the preferred embodiment of the invention has been illustrated and described herein, it is intended to be understood by those skilled in the art that various modifications and omissions in form and detail may be made without departing from the spirit and scope of the invention as defined by the following claims.

What is claimed:

1. A breast pad for nursing mothers comprising a pad body that includes a permeable layer, a substantially waterproof layer, and absorbent material; said body having absorbent portions formed by portions of said layers having said absorbent material sandwiched therebetween, and shaping portions formed by other portions of said layers contiguous to and laminated directly to each other without absorbent material therebetween; said absorbent portions having a first thickness, and said shaping portions having a second thickness less than said first thickness; said absorbent portions including a substantially circular center portion of said body and a plurality of lobes extending radially outwardly from said center portion to an outer perimeter portion of said body, and said shaping portions including a plurality of sections extending radially inwardly from an outer edge of said body between said lobes, with one section being between each pair of adjacent lobes; said body having a substantially flat pre-use configuration, and said sections being sized and shaped and having sufficient flexibility to allow said body to be folded along said sections to shape said body into a convex use configuration which substantially conforms to the shape of a breast and in which said absorbent portions are maintained at a substantially uniform thickness and each said section remains between the corresponding pair of adjacent lobes in a direction defined by a line extending around an outer face of said body radially between said center portion and said perimeter portion and substantially parallel to said outer edge, to maintain a smooth outer contour of a bra of a user of the pad.

2. The breast pad of claim 1, in which said perimeter portion is nonabsorbent, surrounds said absorbent portions, and is formed by edge portions of said layers that are laminated to each other.

3. The breast pad of claim 2, in which each said section of said shaping portions is substantially triangular and tapers radially inwardly from said perimeter portion to said center portion.

4. The breast pad of claim 3, in which said sections are arranged in a plurality of opposite pairs.

5. The breast pad of claim 1, in which each said section of said shaping portions is substantially triangular and tapers radially inwardly from said perimeter portion of said body to said center portion.

6. The breast pad of claim 5, which said sections are arranged in a plurality of opposite pairs.

* * * * *

UNITED STATES PATENT AND TRADEMARK OFFICE
CERTIFICATE OF CORRECTION

PATENT NO: 5,683,286

DATED: November 4, 1997

INVENTOR(S): Laura J. Kielland

It is certified that error appears in the above-identified patent and that said Letters Patent is hereby corrected as shown below:

Claim 6, column 4, line 36, "which" should be -- in which --.

Signed and Sealed this

Tenth Day of March, 1998

Attest:

BRUCE LEHMAN

Attesting Officer

Commissioner of Patents and Trademarks